United States Patent

Moller et al.

Patent Number: 5,171,687
Date of Patent: Dec. 15, 1992

[54] APPARATUS FOR CULTURING AND DELIVERY OF MICROBE FOR WASTE TREATMENT IN A FLOW SYSTEM

[76] Inventors: Erik R. Moller; Ralph O. Moller, both of 9 La Rancheria, Carmel Valley, Calif. 93924

[21] Appl. No.: 580,032

[22] Filed: Sep. 10, 1990

[51] Int. Cl.⁵ .................. C12M 3/02; C12M 1/04; C02F 3/00
[52] U.S. Cl. ................... 435/286; 435/284; 435/302; 435/309; 435/313; 435/813; 210/601; 210/610; 210/205
[58] Field of Search ............... 435/284–287, 435/296, 302, 309, 310, 313, 813; 210/601, 610, 205, 608, 615; 239/310

[56] References Cited

U.S. PATENT DOCUMENTS

| | | | |
|---|---|---|---|
| 3,145,087 | 8/1964 | Walker | 239/310 |
| 3,864,090 | 2/1975 | Richards | 239/310 |
| 4,237,003 | 12/1980 | El-Sayed | 210/610 |
| 4,670,149 | 6/1987 | Francis | 210/608 |
| 4,810,385 | 3/1989 | Hater et al. | 210/610 |
| 4,882,059 | 11/1989 | Wong et al. | 166/65.1 |
| 4,925,564 | 5/1990 | Francis | 210/610 |

OTHER PUBLICATIONS

Roszak et al., Microbiol. Rev., 51, pp. 365–379, 1987.
GES Brochure: Applied Biotechnology In Wastewater Treatment; The LLMO Systems.
Ecolab-St. Paul, Minn.-Biological Grease Digestant For Drains & Grease Traps.

Primary Examiner—James C. Housel
Assistant Examiner—William Chan
Attorney, Agent, or Firm—Theodore J. Bielen, Jr.

[57] ABSTRACT

A apparatus for injecting a solid microbial matter suspended in a liquid into a flow system utilizing a container having first and second chambers. The contents of the first chamber flows through an outlet and into a second chamber. The source microbial matter is supported in the first chamber and water is directed to the first chamber at a predetermined rate. The first chamber is maintained as a nutrient rich environment for the microbial matter while the second chamber is nutrient deficient. The outlet of the second chamber is directed to a flow system benefiting from the activity of the microbial matter.

7 Claims, 3 Drawing Sheets

FIG_2

APPARATUS FOR CULTURING AND DELIVERY OF MICROBE FOR WASTE TREATMENT IN A FLOW SYSTEM

BACKGROUND OF THE INVENTION

The present invention relates to a novel and useful mechanism for injecting solid microbial matter suspended in a liquid into a flow system.

It is known that microbes, such as bacteria are capable of consuming undesirable matter such as sludge, grease, oil, and the like. In general, the bacteria generally break down the undesirable matter into more useful chemical components.

Animal fat and grease often block drains and produce a heavy scum which floats on top of the water present in septic tanks and the like. Moreover, a trap is employed by restaurants to contain this scum layer which must be skimmed periodically to prevent fats and greases from entering a municipal sewage system. It has been found that many bacteria break down fat and grease by splitting the fatty acids from the glycerol part of the fat and grease molecules. The fatty acids dissolve in water possessing a neutral pH in the presence or absence of oxygen. Where oxygen is present, the fatty acids may then be converted to carbon dioxide via a complex series of reactions. In certain cases, the fatty acids may be converted in the presence of oxygen to components needed for the growth of bacterial cells. The glycerol molecules may also be used as an energy source for growth under anaerobic conditions by aerobacter. In addition, under aerobic conditions aerobic bacteria will metabolize the glycerol. In essence, under aerobic conditions such bacteria will transform fat into carbon dioxide and cellular components.

In the past, bacteria in a liquid medium have been placed in a container and slowly pumped into a drain or grease trap for the purpose of grease removal. For example, the automatic drain relief ADR systems distributed by EcoLab of St. Paul Minnesota employs such liquid bourne bacteria. Although partially successful, such system requires a constant resupply of the bacterial component which is impractical in restricted spaces, ie: under a restaurant sink. In addition, it is believed that the direct injection of such liquid bourne bacteria does not maximize enzyme production, which is directly related to fat and grease consumption by the bacteria.

A delivery system which overcomes the problems found in the prior art would be a great advance in the waste management field.

SUMMARY OF THE INVENTION

In accordance with the present invention a novel and useful mechanism or apparatus for injecting solid microbial matter into a flow system is herein provided.

The mechanism of the present invention utilizes first and second chambers which are arranged such that the contents of the first chamber will gravity flow into the second chamber. Matter egressing from the second chamber would be injected into the flow system. The dual chambers may be provided by a single container having the requisite baffling or by separate containers placed adjacent or within one another.

The solid microbial matter, generally in the form of an anaerobic or aerobic bacteria, is placed in the first chamber of the present mechanism. A porous basket may be employed in this regard and be fixed to the walls of the first chamber. Water is then injected into the first chamber by appropriate means and at a pre-determined rate. Simultaneously, oxygen is also injected into the first chamber by bubbling air therewithin. Nutrients for the microbial matter are also included in the first chamber. In certain cases, bacterial nutrients may be formed into a single solid or gel cake with the bacterial component and placed in the first chamber.

A second chamber is also found in the present invention and receives the overflow contents of the first chamber via the outlet of the first chamber. The first chamber may be constructed with means for breaking foam o the surface of the contents of the first chamber. The second chamber is nutrient free in that the nutrients are not injected therein apart from the nutrients which may overflow from the first chamber. It is believed that the dual chamber arrangement of the present mechanism enhances production and activity of bacterial enzymes. Thus, the outlet of the second chamber is injected into the particular flow system, such as the grease trap, of a restaurant facility. Bacterium will then consume the fat and grease found in such trap reducing the need for skimming of the same. The second chamber may also be oxygenated.

A valve may be employed to control the rate of water provided to the first chamber, as well as, the rate of injection of bacteria from the second chamber and into the flow system. Such pre-determined rate should coincide with the activation time of the particular bacterium.

It may be apparent that a novel and useful mechanism for injecting solid microbial matter into a flow system has been described.

It is therefore an object of the present invention to provide a mechanism for injecting a solid microbial matter into a flow system which breaks down animal fat and grease normally found in a waste system.

It is another object of the present invention to provide a mechanism for injecting solid microbial matter into a flow system which greatly increases the time between skimming operations ordinarily accomplished with respect to a grease trap or waste container.

Yet another object of the present invention to provide a mechanism for injecting solid microbial matter into a flow system which decreases the potential amount of grease and animal fat which could pass into a municipal sewage system or municipal dumping site.

Another object of the present invention is to provide a mechanism for injecting solid microbial matter into a flow system which is compact and relatively reliable.

Yet another object of the present invention is to provide a mechanism for injecting solid microbial matter into a flow system which maximizes the enzyme activity of a particular bacterium.

The present invention possesses other objects and advantages which will become apparent as the specification continues.

Figure 1:
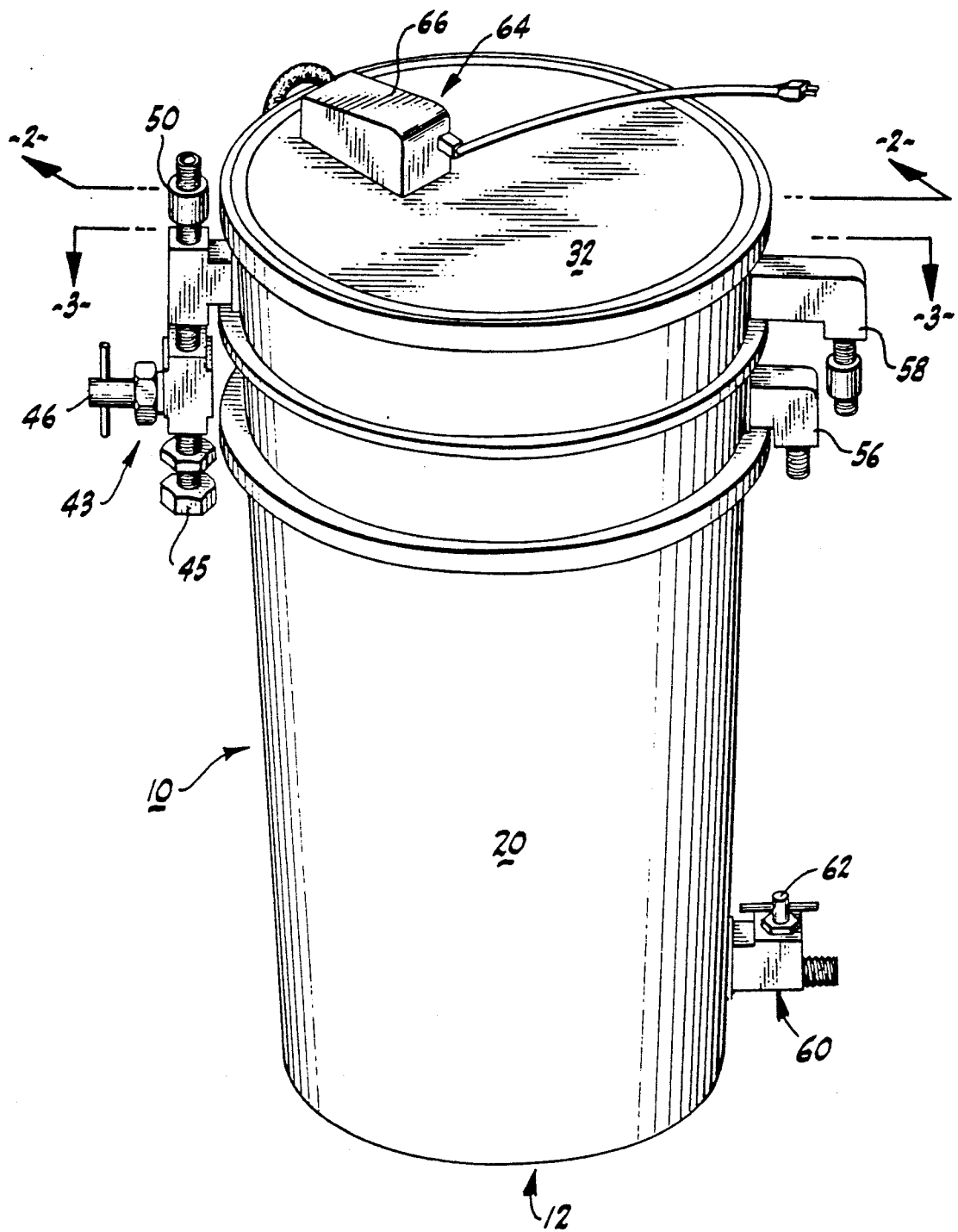
FIG. 1 is a top perspective view of the mechanism of the present invention.

For a better understanding of the invention reference is made to the following detailed description of the preferred embodiments thereof which should be referenced to the hereinabove described drawings.

DESCRIPTION OF THE PREFERRED EMBODIMENTS

Various aspects of the present invention will evolve from the detailed description of the preferred embodiments which should be taken in conjunction with the prior described drawings.

The invention as a whole is shown in the drawings by reference character 10. The mechanism 10 includes as one of its elements a container 12 having a first chamber 14 and a second chamber 16, FIG. 2. Container 12 includes a bottom portion 18 and an upwardly extending side portion 20, forming a generally cylindrical body. First chamber 14 is formed by a another container 22 having a bottom portion 24 and side wall portion 26 which extends upwardly. A circular spacer 28 separates bottom 18 of container 12 from bottom 24 of container 22. It should be apparent that containers 12 and 24 may be integrally formed such that side wall portion 26 takes the form of a baffle within container 12. As depicted in the embodiment shown in FIG. 2, first chamber 14 is cylindrical while second chamber 16 is annular. First chamber 14 includes an outlet 28 and means 30 for dispersing or breaking any foam formed within first chamber 14. Means 30 is found at outlet 28 atop wall portion 26 of container 22. A cover 32 is employed to enclose container 12 and chambers 14 and 16.

Figure 2:
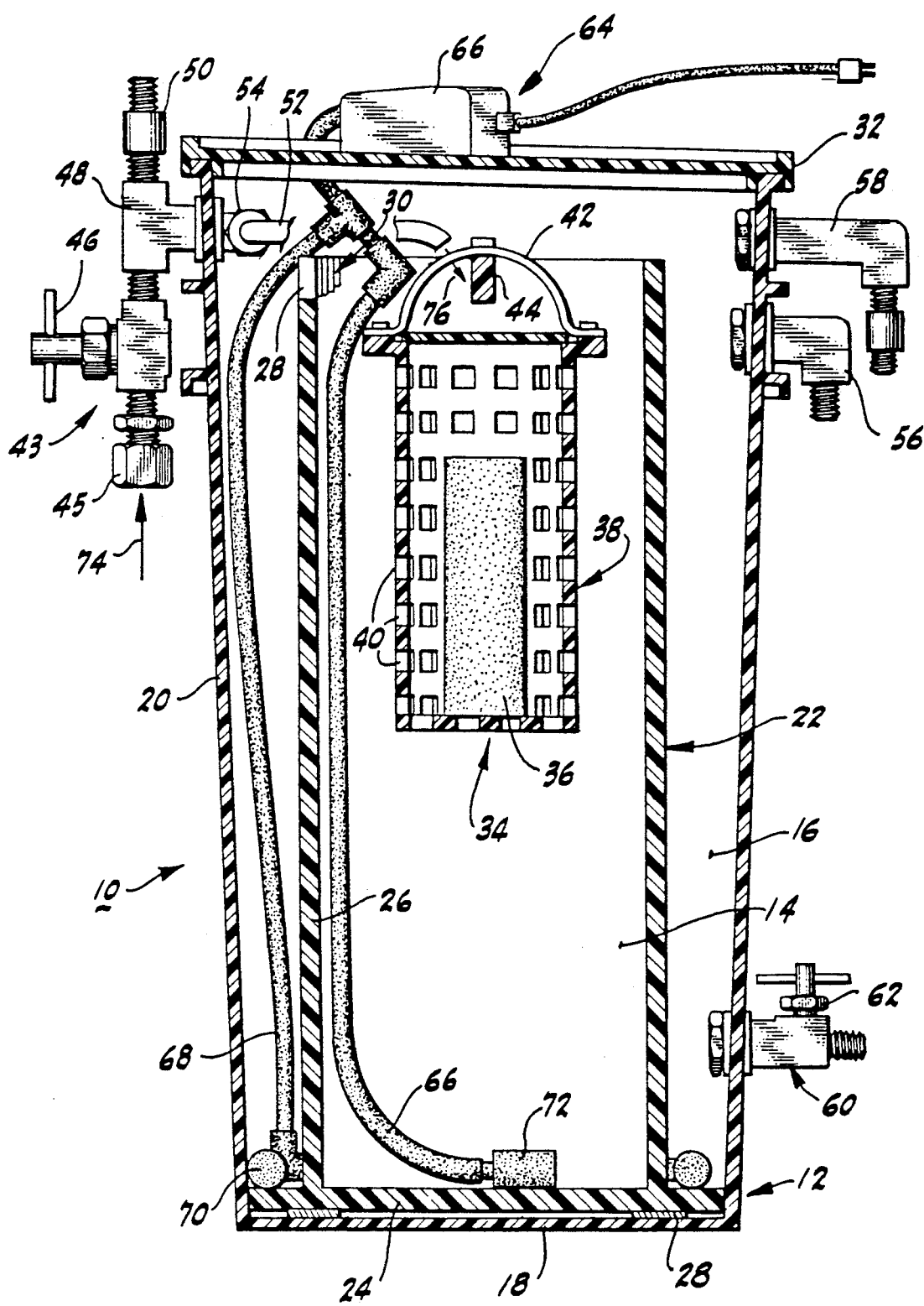
FIG. 2 is a view taken along line 2—2 of FIG. 1.

Means 34 is shown in FIG. 2 for supporting microbial matter 36 within chamber 14. Microbial matter may be a bacterium known as LLMO G1 in a solid or gel form, which is manufactured by General Environmental Science, of Beachwood, OH and available as LLMO G1 gel cube from Envirogenics of Carmel Valley, CA. The bacterial gel 36 includes a grease or fat consuming bacterium, as well as an activator and nutrient for the bacterium. In the embodiment shown, where the combined capacity of chambers 14 and 16 equal about 6 gallons, Bacterial cake 36 has a volume of approximately 30 cubic inches and substitutes for approximately 200 gallons equivalent bacteria in a liquid medium. Bacterial cake or gel 36 is placed in a basket 38 which includes a plurality of openings 40. A bail 42 connects to the top portion of basket 38 and extends over a bar 44 which spans the inner top portion of container 12. Bail 42 is removable from basket 38 such that bacterial cake 36 is accessible.

Means 42 provides water to first chamber 14. Means 42 includes a fitting 44 which connects to a municipal source of water through a hose or other conduit (not shown). Needle valve 46 regulates the flow of water into chamber 14 through tee fitting 48 having an antisyphon nipple 50. Conduit 52 extends into chamber 14 via elbow fitting 54 which passes through the wall of container 12. Fitting 56 serves as outlet from chamber 16 and lies below the level of outlet 28 of first chamber 14. Overflow draw 58 performs the function of a safety outlet from chamber 16. In addition, maintenance draw 60 includes a valve 62 which permits the draining of chamber 14 to a low level.

Means 64 injects oxygen into first and second chambers 14 and 16. Means 64 is constructed with a diaphragm air pump 66 requiring a standard AC electrical source (not shown). Air conduits 66 and 68 extend to the bottom portions of chambers 14 and 16 and include spargers 70 and 72 to disperse the oxygen containing air throughout the liquids normally found in chambers 14 and 16.

Figure 3:
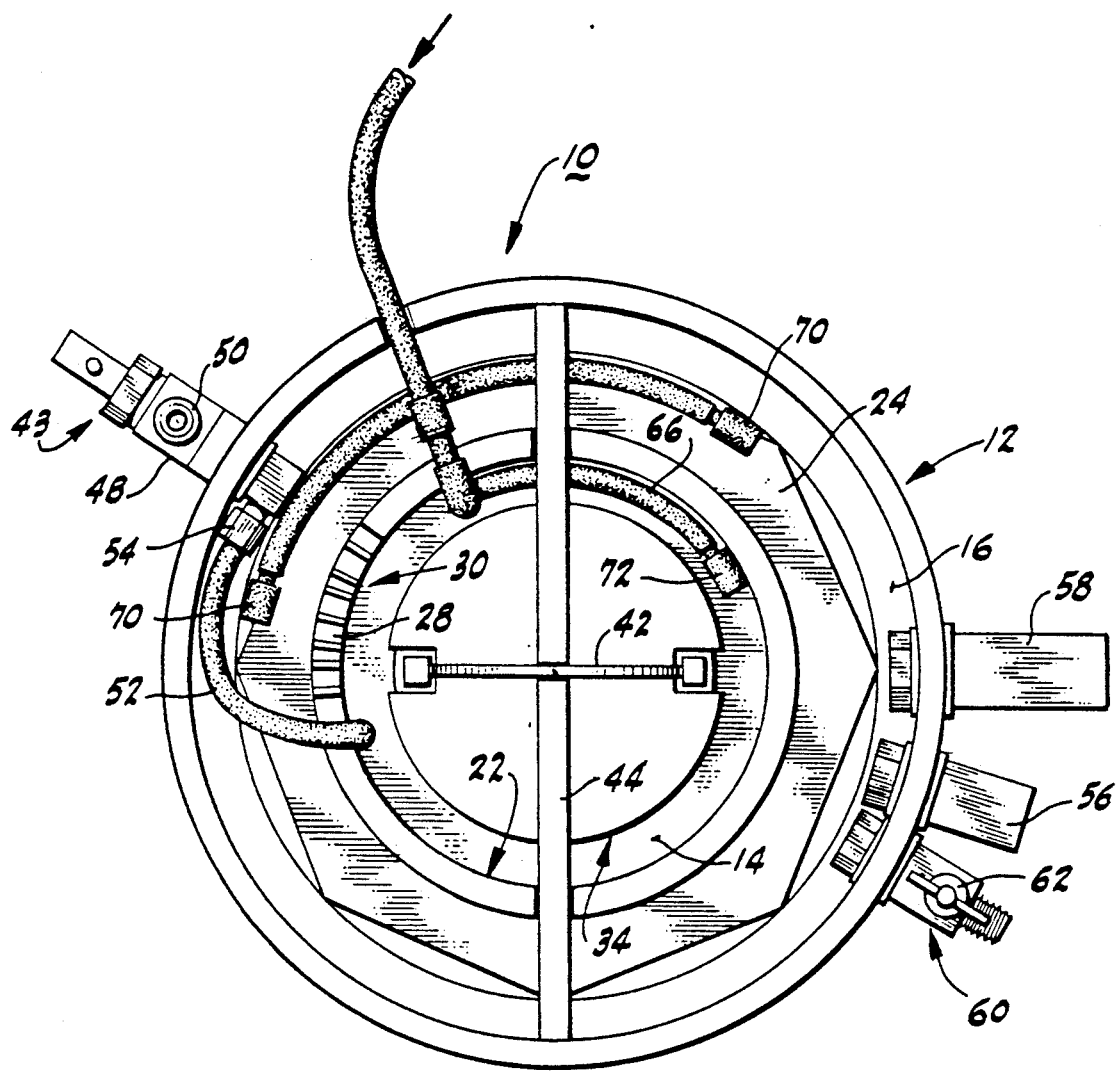
FIG. 3 is a sectional view taken along line 2—2 of FIG. 3.

In operation, the user places bacterium cake 36 within basket 38 and supports basket 38 within chamber 14 of container 12 by the use of bail 42 and bar 44. Cover 32 is then placed atop container 44. Outlet 56 of second chamber 16 is connected to a drain leading into a grease trap or sump or into the sump directly. Needle valve 46 is then opened to control the rate of water entering first chamber 14, directional arrows 74 and 76, FIGS. 2 and 3. Air is then fed into container 12 by activating means 64 through the functioning of pump 66, FIGS. 1 and 2. Water slowly fills chamber 14 until reaching outlet 28. At this point the bacteria within chamber 14 has been activated by nutrients supplied either through bacterium cake 36 or through an external source. Bacteria entering chamber 16 passes or transports into a relatively nutrient-free environment and remains in chamber 16 until the water level in chamber 16 reaches outlet 56. At this point, the enzymes produced by the bacteria are particularly active. Such bacteria are then fed to a flow system such as a drain leading into a grease sump for use therein. It is believed that starving the bacteria of nutrients in chamber 16 activates enzyme production therein. It has been found that feeding the nutrient rich bacteria directly from first chamber 14 to the flow system decreases the effectiveness of the bacteria by 50%. Also, the flow rate determined by valve 46 is generally adjusted to coincide with the peak activation time associated with the bacterium found in the cake 36. In the present system it has been determined that approximately a rate of 6 gallons per day produces excellent results in the present embodiment. Thus, the bacterium maintains residence in first chamber 14 or approximately 12 hours and in second chamber 16 for approximately 12 hours. However, the sizes of chambers 14 and 16 as well as the rate of water and air fed into the same, may be adjusted according to the particular bacterium used in basket 38.

While, in the foregoing embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. An apparatus for continuously injecting bacterial matter into a flow system comprising:
    a. a container having a first chamber, said first chamber having an outlet;
    b. means of providing the bacterial matter in said first chamber;
    c. means for providing water to said first chamber at a predetermined rate;
    d. means for providing oxygen to said first chamber;
    e. means of providing nutrients for the bacterial matter in aid first chamber;
    f. said container providing a second chamber having an outlet, said second chamber common indicating with said first chamber owlet to permit transport of said water and bacterial; matter in said first chamber to said second chamber, said second chamber being nutrient deficient relative to said first chamber; and
    g. means for transporting said water and bacterial matter in said second chamber to the flow system at a predetermined rate through said second chamber outlet.

2. The apparatus of claim 1 which additionally comprises means for providing oxygen to said second chamber.

3. The apparatus of claim 1 in which said first chamber outlet is at a higher level than said second chamber outlet to permit gravity flow of said contents of said first chamber to said second chamber.

4. The apparatus of claim 1 in which said means of providing water to said first chamber past a predetermined rate includes a valve, said valve further controlling said predetermined transport rate of said water and bacterial mater in said second chamber to said flow system.

5. The apparatus of claim 3 which additionally comprises means for breaking foam on the surface of the contents of said first chamber, said contents being transported to said second chamber.

6. The apparatus of claim 1 in which said rate of transport of said contents of said second chamber substantially equals said rate of provision of water to said first chamber.

7. The apparatus of claim 1 in which said second chamber surrounds the first chamber in an annular configuration.

* * * * *